(12) United States Patent  
Shimamoto

(10) Patent No.: US 7,247,652 B2
(45) Date of Patent: Jul. 24, 2007

(54) β-BENZYLOXYASPARTATE DERIVATIVES WITH AMINO GROUP ON BENZENE RING

(75) Inventor: Keiko Shimamoto, Osaka (JP)

(73) Assignee: Suntory Limited, Osaka (JP)

( * ) Notice: Subject to any disclaimer, the term of this patent is extended or adjusted under 35 U.S.C. 154(b) by 185 days.

(21) Appl. No.: 10/481,237

(22) PCT Filed: Jun. 24, 2002

(86) PCT No.: PCT/JP02/06286

§ 371 (c)(1),
(2), (4) Date: Jul. 19, 2004

(87) PCT Pub. No.: WO03/000698

PCT Pub. Date: Jan. 3, 2003

(65) Prior Publication Data

US 2004/0242652 A1 Dec. 2, 2004

(30) Foreign Application Priority Data

Jun. 22, 2001 (JP) ............................. 2001-190022

(51) Int. Cl.
A61K 31/235 (2006.01)
A61K 31/255 (2006.01)
A61K 31/195 (2006.01)
C07C 69/76 (2006.01)
C07C 69/34 (2006.01)
C07C 229/00 (2006.01)

(52) U.S. Cl. .............. 514/533; 514/547; 514/561; 514/567; 560/88; 560/196; 562/444; 562/568

(58) Field of Classification Search .............. 514/533, 514/547, 561, 567; 560/88, 196; 562/444, 562/568
See application file for complete search history.

(56) References Cited

U.S. PATENT DOCUMENTS 6,147,113 A * 11/2000 Shimamoto et al. ........ 514/533

FOREIGN PATENT DOCUMENTS

EP 0658539 6/1995
EP 0844234 5/1998

OTHER PUBLICATIONS

DL-threo-B-Benzyloxyaspartate, A Potent Blocker of Excitatory amino acid transporters, Molecular Pharmacology, 1998, vol. 53(2), pp. 195-201, especially p. 197.*
Shimamoto, et al., Mol. Pharm., vol. 53, pp. 195-201, especially p. 195 (1998).*
Arriza J.L. et al. "Functional Comparisons of Three Glutamate Transporter Subtypes Cloned From Human Motor-Cortex" J. of Neuroscience, vol. 14, No. 9, Sep. 1, 1994.
Lebrun B. et al. "New Beta-Hydroxyasparate Derivatives . . . Glutamate/Asparate Transporter" J. of Biological Chemistry, vol. 272, No. 33, Aug. 15, 1997, pp. 20336-20339.

* cited by examiner

Primary Examiner—Joseph K. McKane
Assistant Examiner—Susannah L. Chung
(74) Attorney, Agent, or Firm—Paul E. White; Manelli Denison & Selter PLLC

(57) ABSTRACT

L-threo-β-benzyloxyaspartate derivatives having a substituent on the benzene ring, represented by the following formula (1):

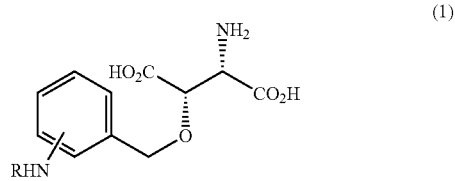

(1)

wherein R is hydrogen, a linear or branched lower aliphatic acyl group with the acyl portion optionally substituted, an alicyclic acyl group, an aromatic acyl group with a substituent on the aromatic ring, an amino acid-derived group or a biotin derivative-derived group,
having an amino substituent on the benzene ring, and salts thereof, which can easily bind to affinity column chromatography carriers as ligands of glutamate transporter proteins.

15 Claims, No Drawings

β-BENZYLOXYASPARTATE DERIVATIVES WITH AMINO GROUP ON BENZENE RING

This application is the national phase of international application PCT/JP02/06286 filed 24 Jun. 2002 which designated the U.S.

TECHNICAL FIELD

The present invention relates to L-glutamate uptake inhibitors, and more specifically, it relates to derivatives of optically active L-threo-β-benzyloxyaspartate having an amino substituent on the benzene ring, represented by the following formula (1) and having activity which inhibits uptake of glutamate by L-glutamate transporters.

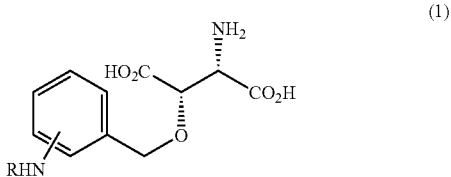

(1)

wherein R is hydrogen, a linear or branched lower aliphatic acyl group with the acyl portion optionally substituted, an alicyclic acyl group, an aromatic acyl group with a substituent on the aromatic ring, an amino acid-derived group or a biotin derivative-derived group.

Development of these compounds constitutes a starting point for the development of inhibitors of glutamate uptake by L-glutamate transporters, and is expected to lead to treatment for neuropathic disorders and neurodegenerative diseases such as epilepsy, Huntington's disease, amyotrophic lateral sclerosis (ALS) and Alzheimer's disease.

BACKGROUND ART

L-glutamate is a excitatory neurotransmitter found in the central nervous system of mammals, and it is known not only to induce rapid neurotransmission between synapses but also to be involved on a higher level in the complex physiological processes of memory and learning. Excitatory neurotransmission between synapses begins with release of glutamate from the presynapse, and fades with rapid glutamate uptake from the synaptic cleft by high-affinity glutamate transporters found in nerve endings and glial cells (Attwell, D. and Nicholls, D., TIPS 68-74, 1991).

Reduced sodium-dependent glutamate uptake activity in portions of patient brains has been reported in several genetic neurodegenerative diseases (Rothstein, J. D. et al., N. Eng. J. Med. 326, 1464-1468, 1992). For this reason, activation and inhibition of glutamate transporter function are becoming objects of focus in connection with such diseases.

In initial steps of research, study of glutamate transporters was carried out primarily using synaptosomes prepared from brain tissue or membrane specimens from the kidney and small intestine. Later, after cloning of sodium-dependent high-affinity glutamate transporter cDNA in 1992, research was conducted from a molecular biological perspective (Pines, G. et al., Nature 360, 464-467, 1992; Storck, T. et al., Proc. Natl. Acad. Sci. USA, 89, 10955-10959, 1992; Kanai, Y. et al., Nature 360, 467-471, 1992). In 1994, the human glutamate transporter gene was cloned and five subtypes, EAAT1 to EAAT5, were categorized (Arriza, J. L. et al., J. Neurosci. 14, 5559-5569; Fairman, W. A. et al., Nature, 375, 599-603, 1995; Arriza, J. L. et al., Proc. Natl. Acad. Sci. USA 94, 4155-4160, 1997).

However, given the low homology of glutamate transporter protein with other neurotransmitter transporters and the difficulty of inferring transmembrane regions based on hydrophobisity, there is still disagreement regarding the 3-dimensional structure and substrate recognition site structure (Grunewald, M. et al., Neuron 21, 623-632, 1998; Seal, R. P. et al., Neuron 25, 695-706, 2000).

In light of these circumstances, it is desirable to develop various glutamate transporter inhibitors, and especially inhibitors that function as blockers, toward elucidation of the relationship between the glutamate transporter family and neuropathic disorders and neurodegenerative diseases such as epilepsy, Huntington's disease, amyotrophic lateral sclerosis (ALS) and Alzheimer's disease.

As a result of investigation for glutamate uptake inhibitors using synaptosomes according to the prior art, compounds such as threo-β-hydroxyaspartate and CCG-III [(2S,1'S, 2'R)-2-(carboxycyclopropyl)glycine], t-2,4-PDC (trans-pyrrolidine-2,4-dicarboxylic acid) and the like have hitherto been identified as glutamate uptake inhibitors, and these are themselves taken up as substrates by transporters and thus act as inhibitors that competitively inhibit glutamate uptake.

The glutamate uptake inhibitors such as kainic acid and dihydrokainic acid were demonstrated by electrophysiological studies to be blockers that inhibit glutamate uptake without themselves being taken up. It was further shown that these compounds act only on EAAT2 (GLT-1 type) of the five EAAT subtypes (Arriza, J. L. et al., J. Neurosci. 14, 5559-5569, 1994). Nevertheless, these compounds have also exhibited strong excitatory effects on ion-channel glutamate receptors.

The present inventors have reported that β-hydroxyaspartate derivatives having substituents at the β-position exhibit an uptake-inhibiting effect for all of the five EAAT subtypes (Lebrun, B. et al., J. Biol. Chem. 272, 20336-20339, 1997; Shimamoto, K. et al., Mol. Pharmacol. 53, 195-201, 1998; Shigeri, Y. et al., J. Neurochem. 79, 297-302, 2001). Among them, it was found that compounds with bulky substituents at the β-position act as blockers for all of the subtypes, inhibiting not only uptake of glutamate but also heteroexchange-based glutamate efflux and sodium ion influx (Chatton, J-Y. et al., Brain Res. 893, 46-52, 2001). In particular, L-threo-β-benzyloxyaspartate (L-TBOA), because of its powerful blocking effect and its lower affinity for glutamate receptor compared to existing inhibitors, has become a standard substance used in glutamate transporter research.

SUMMARY OF THE INVENTION

Four stereoisomers of β-hydroxyaspartate exist, and it is the L-threo form that exhibits the strongest uptake inhibition among them (Shimamoto, K. et al., Bioorg. Med. Chem. Lett. 10, 2407-2410, 2000). The conventional TBOA is used in the DL form, but it has been desired to accomplish selective synthesis of the L-threo form in order to properly investigate the structure/activity relationship.

At the same time, protein purification is essential for elucidating the 3-dimensional structure of the glutamate transporter and shedding light on the substrate transport mechanism and substrate-binding site. And affinity column chromatography is an effective means of protein purification. Protein purification using antibodies has already been attempted, but this has been inconvenient because the strong binding between the antibodies and the protein results in loss of the original protein function upon elution. Using a blocker as the affinity column ligand would allow elution under mild conditions, and therefore blockers having substituents that can bind to affinity columns have also been a target of research.

DETAILED DESCRIPTION OF THE INVENTION

The present inventors focused on the strong affinity of TBOA, and considered synthesizing TBOA derivatives with a substituent on the benzene ring and allowing the substituent to bind to the column carrier. Upon extensive research aimed at selectively synthesizing L-threo-hydroxyaspartate derivatives, we invented a synthesis pathway whereby desired L-threo-benzyloxyasparatate derivatives can be obtained using optically active epoxide as the starting material, and found that β-benzyloxyaspartate derivatives having an amino group on the benzene ring retain uptake inhibiting activity even when substitution occurs on the amino group.

Compounds having acyl groups as substituents function as glutamate transporter inhibitors with inhibiting action equivalent to or exceeding that of TBOA. In particular, compounds having a benzoyl derivative were found to exhibit vastly increased activity and were superior to TBOA as inhibitors. On the other hand, compounds having amino acids as substituents permit ready binding between the free amino groups and carboxylic or halogenated alkyl groups of commercially available column carriers. Alternatively, compounds with biotinyl groups allow binding with commercially available avidin columns. It was thus found that these compounds allow sufficient binding to column carriers while maintaining blocker activity, and the present invention was thereby completed. In other words, the present invention provides derivatives of optically active β-benzyloxyaspartate having an amino substituent on the benzene ring, represented by chemical formula (1), and salts thereof, as glutamate transporter blockers and as affinity column ligands.

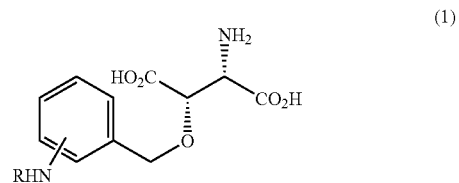

wherein R is hydrogen, a linear or branched lower aliphatic acyl group with the acyl portion optionally substituted, an alicyclic acyl group, an aromatic acyl group with a substituent on the aromatic ring, an amino acid-derived group or a biotin derivative-derived group.

More specifically, in formula (1), R is hydrogen, a linear or branched $C_1$-$C_8$ lower aliphatic acyl group, a $C_4$-$C_8$ alicyclic acyl group, a $C_5$-$C_{15}$ aromatic acyl group, an amino acid derivative or a biotin derivative. Examples of linear or branched lower aliphatic and alicyclic acyl groups represented by R include acetyl, propionyl, n-butanoyl, sec-butanoyl, n-pentanoyl, pivaloyl, phenylacetyl and cyclohexylcarbonyl. Substituents may also be present on the acyl group and examples of substtituents include hydroxyl group, thiol group, amino group and carboxyl group. Examples of aromatic acyl groups represented by R include benzoyl, naphthoyl and pyridylcarbonyl. Substituents may also be present on the aromatic ring. Examples of substituents on the aromatic ring include linear or branched $C_1$-$C_7$ alkyl, $C_4$-$C_{10}$ aryl, $C_1$-$C_6$ alkoxyl, nitro, cyano, amino, $C_1$-$C_7$ acylamino, carboxyl, halogen, halogenated $C_1$-$C_6$ alkyl, biotinyl, and biotinylalkyl with the alkyl portion being $C_1$-$C_6$, and the like. Examples of amino acids represented by R include glycyl, alanyl, β-alanyl and cysteinyl. Examples of biotin derivatives represented by R include biotinyl and biotinyl-β-alanyl.

The compounds of the invention may be obtained as salts by ordinary methods. Alkali metal salts such as sodium salts and potassium salts and alkaline earth metal salts such as calcium salts, as well as ammonium salts, are all included as such salts according to the invention. Salts may also be obtained with ordinary acids. Inorganic acid salts such as hydrochloric acid salts and sulfuric acid salts, and organic acid salts such as acetic acid salts, citric acid salts and trifluoroacetic acid salts are also included as such salts according to the invention.

The position of the substituent on the benzene ring may be any one of the three positions of ortho-, meta- or para-, according to the invention. However, study of the structure/activity relationship of the compounds has revealed that in the case where an amino group is positioned on the benzene ring, the meta-position of the amino group provides strongest activity. The synthesis scheme below, therefore, shows examples of introduction for obtaining compounds with substituents at the meta-position; nevertheless, agents with different substitution patterns may be used for introduction of desired substituents.

The compounds of the invention may be synthesized in the following manner. For example, compounds wherein R is β-alanyl, biotinyl-β-alanyl or propionyl-β-alanyl may be synthesized according to the following scheme.

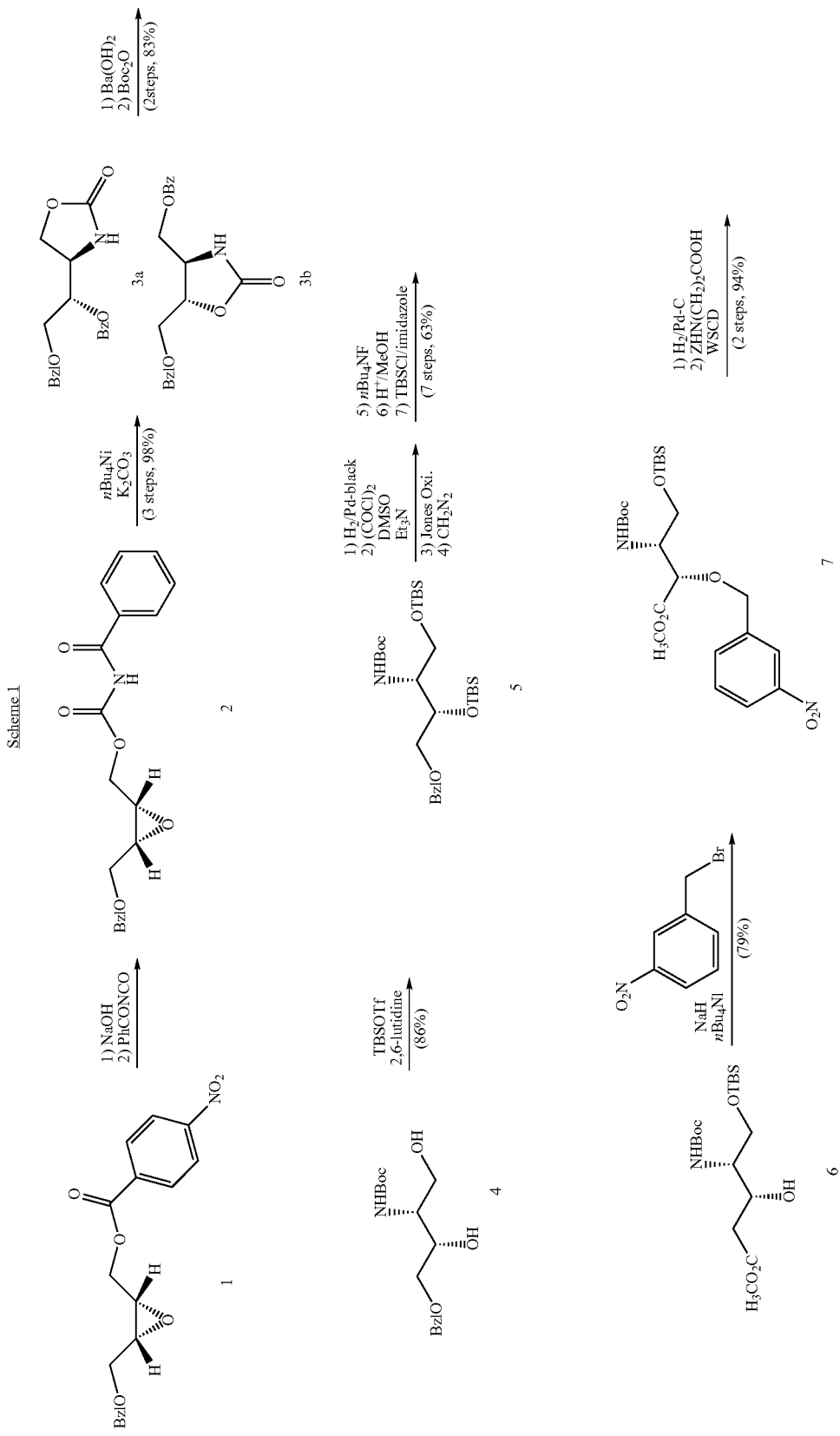

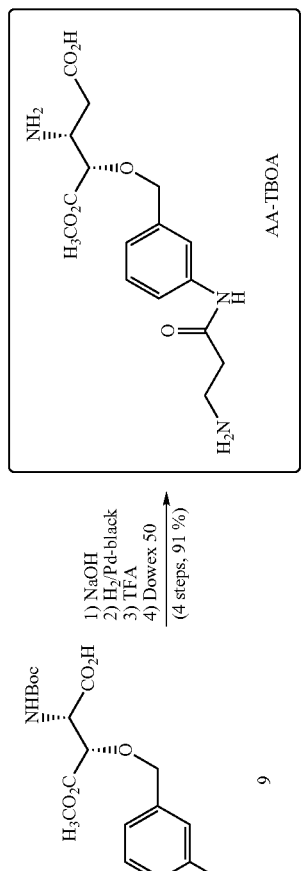
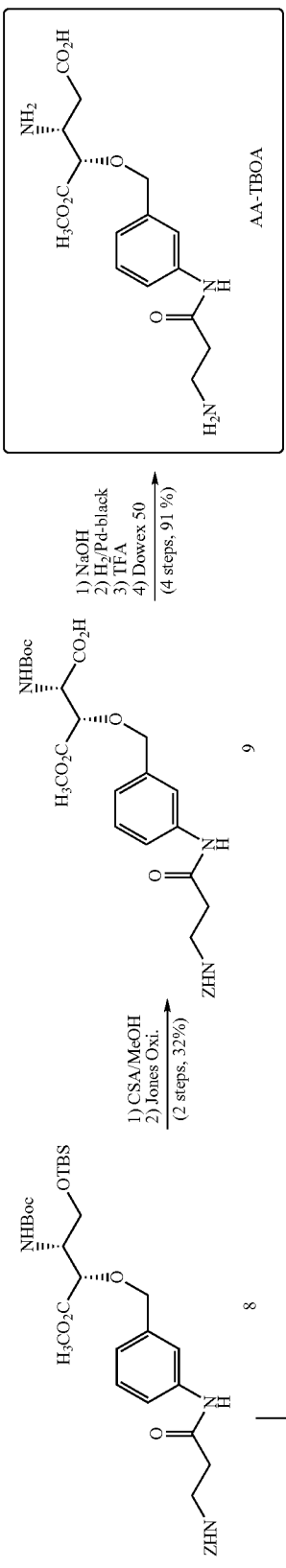
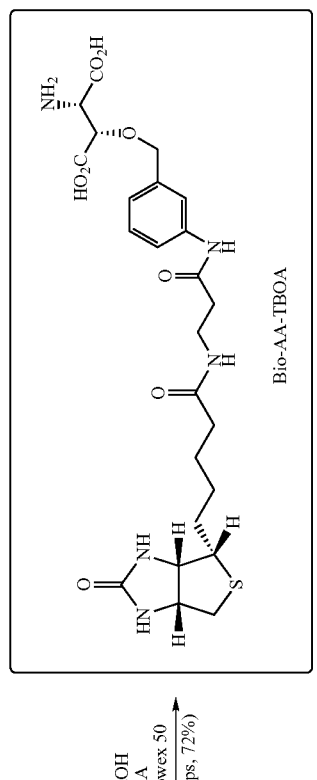
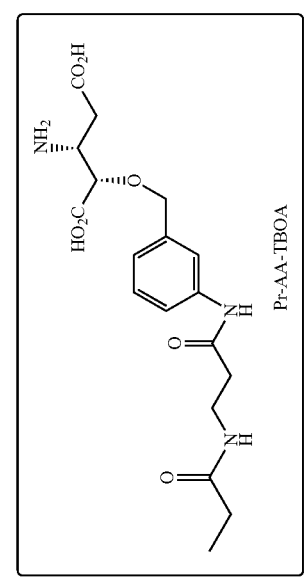

It is a characteristic feature of the synthesis method of the invention that an optically active starting material may be used for compound (1) in the above scheme. The hydroxyl-protecting group of the compound is first removed with an alkali metal hydroxide such as NaOH and then the resulting free hydroxyl group is reacted with a benzoylisocyanate to obtain the benzoylcarbamate represented by formula (2). As the reaction conditions, the benzoylisocyanate is added to a THF (tetrahydrofuran) solution in approximately 1.2 equivalents at room temperature, and the mixture is stirred for about 30 minutes. The compound of formula (2) is reacted in the presence of a catalytic amount of tetrabutylammonium iodide under weakly basic conditions, to produce a mixture of the L-threo cyclocarbamates represented by formula (3a) and formula (3b). As the reaction conditions, potassium carbonate is added at approximately 2 equivalents and tetrabutylammonium iodide in approximately 0.15 equivalent to an acetonitrile solution, and the mixture is stirred at room temperature for from 14 hours to 18 hours.

This synthesis method of the invention selectively yields a L-threo cyclocarbamate mixture as a production intermediate. Methods described in prior art publications (Bioorg. Med. Chem. Lett. 10, 2407-2410, 2000) have required column purification of the threo-form from a mixture containing the erythro-form, but the method of the present invention significantly reduces workload by dispensing with the purification.

For nitrobenzylation, compound (6) was used as the substrate instead of the known lactone intermediate (Bioorg. Med. Chem. Lett. 10, 2407-2410, 2000), in order to suppress isomerization to the erythro-form. While isomerization of about 30% is seen with the conventional substrate, using the present compound results in only trace amounts, rendering it a more threo-selective production method. As the reaction conditions, sodium hydride is added at approximately 1.5 equivalents and tetrabutylammonium iodide at approximately 0.3 equivalent to a DMF solution of compound (6) cooled to about −20° C., and then nitrobenzyl bromide (preferably 3-nitrobenzyl bromide) is added at approximately 1.5 equivalents and the mixture is stirred at about −20° C. for about 30 minutes and then at about 0° C. for about 30 minutes. In this reaction, the yield can be greatly improved by using a nitro group as the amino equivalent, since when a 3-protected-aminobenzyl bromide is used instead of 3-nitrobenzyl bromide, the reaction will not proceed sufficiently even with a prolonged reaction time and an increased temperature. Compound (7) obtained by this reaction can then be easily converted to the corresponding amino compound by reduction of the nitro group. Subsequent acylation by reaction with an acid chloride or carboxylic acid and a condensation agent can convert it to a compound having the desired substituent. Compound (7) is therefore useful as an intermediate for synthesis of the target amino-substituted benzyloxyaspartate.

EFFECT OF THE INVENTION

Well-known methods can be used to determine inhibitory activity of the compounds of the invention on glutamate transporters. For example, the compounds of the invention have been confirmed to inhibit uptake of $^{14}C$-labeled glutamate into cells by human EAAT2 and EAAT3 stably expressed on MDCK (Madin-Darby Canine Kidney) cells or transiently expressed on COS-1 cells. This indicates that the compounds of the invention may play a role in elucidating the glutamate transporter mechanism, and are useful for research on structure/activity relationship, protein structure analysis and the like, in connection with neurodegenerative diseases.

Preparation of Affinity Column

Some of the Compounds of formula (1) may be used as ligands of an affinity column for isolation and/or purification of glutamate transporter proteins. Well-known methods may be used to prepare an affinity column. (For coupling reactions in general, refer to Affinity Chromatography Handbook: Principles and Methods, published by Amersham Pharmacia Biotech; for reactions of biotin derivatives, D. Savage, G. Matton, S. Desai, G. Nielander, S. Morgensen, E. Conklin, Avidin-Biotin Chemistry: A handbook, Pierce Chemical Company (Rockford, USA), 1992.)

Purification of Protein by Affinity Column

A liquid sample suspected of containing a target protein may be introduced into a column prepared as described above. The liquid flow is suspended to incubate the column for a certain period, e.g., about 30 min. The protein is eluted with an elution buffer (e.g., 0.1 M HCl, pH 2.2). If necessary, the protein solution is passed through a desalting column to remove the salt.

Some compounds of formula (1) are useful for radioisotope labeled ligands for identification of transporter proteins. Isotope labeled ligands may be obtained by well known synthetic procedures, using the hydroxybenzoyl intermediate for R group in the formula (1) with the reaction, for example, of labeled methyl iodide to yield the desired labeled ligand as shown in Scheme 2. Some of the radioisotope labeled methyl iodides are commercially available, including, deuterium-labeled methyl iodide, tritium-labeled methyl iodide, Carbon 14-labeld or Carbon 11-labeled methyl iodides.

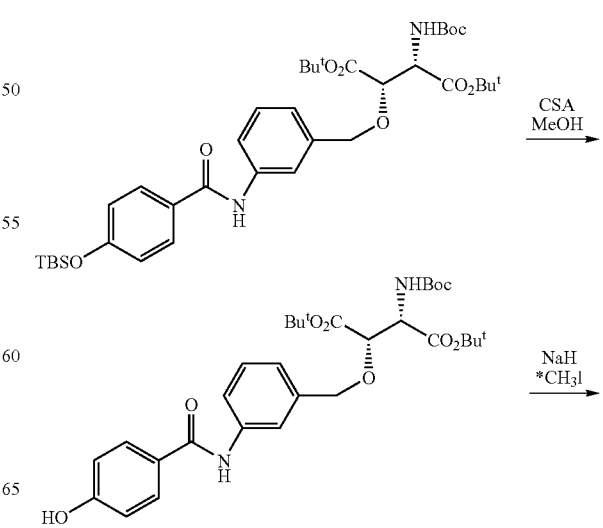

Scheme 2

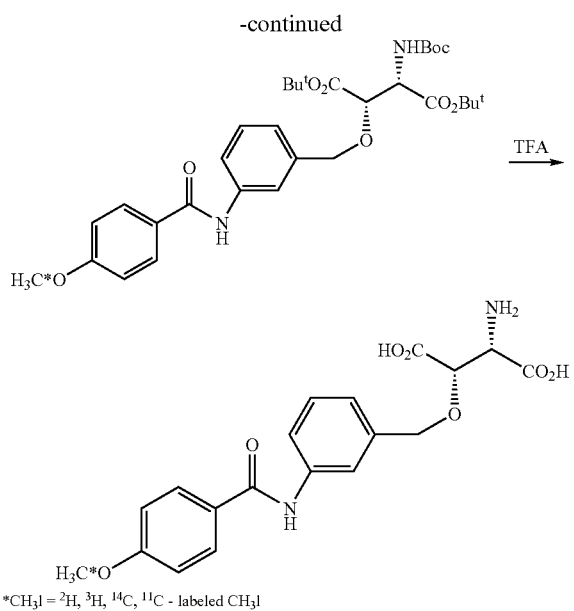

*CH₃I = ²H, ³H, ¹⁴C, ¹¹C - labeled CH₃I

EXAMPLES (2S,3R)-Benzoylcarbamic acid [3-(benzyloxymethyl)oxiranyl]methyl ester (2)

A 1N sodium hydroxide aqueous solution (17.5 mL, 17.5 mmol) was added to a THF solution (20 ml) containing commercially available (2S,3R)-[3-(benzyloxymethyl)oxiranyl]methanol p-nitrobenzoic acid ester (5.0 g, 14.6 mmol), and the mixture was stirred at 0° C. for one hour. The reaction solution was extracted with ether, and the organic layer was washed with water and dried over magnesium sulfate. The solvent was distilled off to obtain an oily alcohol. This was dissolved in THF (20 mL), and a THF solution containing benzoylisocyanate (2.57 g, 17.5 mmol) was added at room temperature. The reaction solution was stirred at room temperature for 30 minutes, and a saturated ammonium chloride aqueous solution was added to quench the reaction. After ether extraction, the organic layer was dried over magnesium sulfate. The solvent was distilled off and the resulting residue was purified by silica gel column chromatography (ether/hexane=3/1) to obtain 5.8 g of the title compound (>100%). This product, though containing a small amount of impurity (benzamide) was used without further purification for the following reaction. A portion thereof was purified by recrystallization (ether/hexane) as an analysis sample.

mp 79-81° C.; $[\alpha]_D$ −22.9° (c 0.80, CHCl₃); ¹H NMR (CDCl₃, 400 MHz); δ3.31 (m 2H), 3.64 (dd, 1H, J=6.0, 11.5 Hz), 3.73 (dd, 1H, J=4.3, 11.5 Hz), 4.15 (dd, 1H, J=7.0, 12.0 Hz), 4.54 (dd, 1H, J=3.5, 12.0 Hz), 4.54 (d, 1H, J=12.0 Hz), 4.61 (d, 1H, J=12.0 Hz), 7.30 (m, 1H), 7.35 (m, 4H), 7.48 (ddd, 2H, J=1.0, 7.5, 7.8 Hz), 7.59 (tt, 1H, J=1.0, 7.5 Hz), 7.83 (ddd, 2H, J=1.0, 1.0, 7.8 Hz), 8.33 (s, 1H).

(4R,1'S)-4-(2-Benzyloxy-1-benzoyloxyethyl)-oxazolidin-2-one (3a)

(4R,5S)-4-benzyloxymethyl-5-benzyloxymethyl-oxazolidin-2-one (3b)

Potassium carbonate (4.04 g, 29.2 mmol) and tetrabutylammonium iodide (800 mg, 2.2 mmol) were added to an acetonitrile solution (100 mL) containing 5.8 g of benzoylcarbamate (2), and the mixture was stirred at room temperature for 18 hours. Saturated ammonium chloride aqueous solution was added to the reaction solution to quench the reaction. After ether extraction, the organic layer was dried over magnesium sulfate. The solvent was distilled off and the resulting residue was purified by silica gel column chromatography (ether/hexane=2/1) to obtain 4.87 g of a mixture of the title compounds (3 steps, 98%).

3a: mp 85-87° C.; $[\alpha]_D$ +43.6° (c 0.55, CHCl₃); ¹H NMR (CDCl₃, 400 MHz); δ3.68 (d, 2H, J=5.0 Hz), 4.11 (ddd, 1H, J=, 4.5, 5.0, 5.5 Hz), 4.27 (dd, 1H, J=5.5, 11.5 Hz), 4.44 (dd, 1H, J=4.5, 11.5 Hz), 4.57 (dt, 1H, J=5.0, 5.0 Hz), 4.58 (d, 1H, J=11.5 Hz), 4.61 (d, 1H, J=11.5 Hz), 6.08 (br s, 1H), 7.33 (m, 5H), 7.43 (ddd, 2H, J=1.0, 7.5, 7.8 Hz), 7.57 (tt, 1H, J=1.0, 7.5 Hz), 8.00 (ddd, 2H, J=1.0, 1.0, 7.8 Hz). 3b: mp 116-117° C.; $[\alpha]_D$ −52.6° (c 0.86, CHCl₃); ¹H NMR (CDCl₃, 400 MHz); δ3.75 (dd, 1H, J=4.5, 10.5 Hz), 3.83 (dd, 1H, J=3.8, 10.5 Hz), 4.24 (dd, 1H, J=4.8, 8.8 Hz), 4.29 (ddd, 1H, J=3.5, 4.8, 8.5 Hz), 4.49 (d, 1H, J=8.5 Hz), 4.51 (d, 1H, J=8.5 Hz), 4.54 (d, 1H, J=8.8 Hz), 5.16 (ddd, 1H, J=3.5, 3.8, 8.5 Hz), 5.98 (s, 1H), 7.29 (m, 5H), 7.44 (m, 2H), 7.58 (tt, 1H, J=1.5, 7.5 Hz), 8.03 (m, 2H).

(2R,3S)-4-benzyloxy-2-N-tert-butoxycarbonylamino-1,3-butanediol (4)

Barium hydroxide (octahydrate) (11.3 g, 35.7 mmol) and water (100 mL) were added to an ethanol solution (100 mL) containing cyclic carbamate (3) (4.05 g, 11.9 mmol), and the suspension was stirred at 80° C. for 18 hours. After cooling on ice, the pH was adjusted to 3 with 10% diluted sulfuric acid. The precipitate was filtered off with celite, the filtrate was concentrated, di-t-butyl-dicarbonate (5.5 mL, 23.8 mmol) and 1,4-dioxane (100 mL) were added and the pH was adjusted to 9 with a 1N sodium hydroxide solution. The reaction mixture was stirred at room temperature for 18 hours and neutralized with 1N hydrochloric acid, after which extraction was performed with ethyl acetate and the organic layer dried over magnesium sulfate. The residue obtained by distilling off the solvent was purified by silica gel column chromatography (ether/hexane=3/1) to obtain 3.06 g of the title compound (2 steps, 83%).

Oily: $[\alpha]_D$ +3.1° (c 0.87, CHCl₃); ¹H NMR (CDCl₃, 400 MHz); δ1.37 (s, 9H), 2.88 (br s, 1H), 3.12 (s, 1H), 3.46 (dd, 1H, J=7.5, 9.5 Hz), 3.53 (dd, 1H, J=4.5, 9.5 Hz), 3.66 (m, 1H), 3.69 (m, 1H), 3.79 (m, 1H), 4.07 (s, 1H), 4.50 (s, 2H), 5.26 (d, 1H, J=7.5 Hz), 7.30 (m, 5H)

(2R,3S)-4-benzyloxy-2-N-tert-butoxycarbonylamino-1,3-bis(tert-butyldimethylsilyloxy)-butane (5)

t-Butyldimethylsilyl trifluoromethanesulfonate (4.4 mL, 19 mmol) and 2,6-lutidine (3.0 mL) were added to a methylene chloride solution (100 mL) containing a diol (4) (2.0 g, 6.4 mmol) while cooling on ice, and the mixture was stirred for 30 minutes. A saturated ammonium chloride aqueous solution was added to quench the reaction, extraction was performed with ether, and the organic layer was washed with 1N hydrochloric acid and a saturated sodium chloride aqueous solution and dried over magnesium sulfate. The solvent was distilled off and the resulting residue was purified by silica gel column chromatography (ether/hexane=1/3) to obtain 2.96 g of the title compound (86%) and 295 mg of a monosilyl compound (11%).

Oily: $[\alpha]_D$ −7.7°(c1.71, CHCl₃); ¹H NMR (CDCl₃, 400 MHz); δ−0.01 (s, 3H), 0.00 (s, 6H), 0.02 (s, 3H), 0.82 (s, 9H), 0.83 (s, 9H), 1.45 (s, 9H), 3.39 (m, 3H), 3.56 (dd, 1H, J=5.0, 10.0 Hz), 3.70 (m, 1H), 4.12 (dt, 1H, J=1.5, 6.0 Hz), 4.44 (s, 2H), 4.71 (d, 1H, J=9.0 Hz), 7.20 (m, 1H), 7.28 (m, 4H).

(2S,3R)-3-tert-Butoxycarbonylamino-4-tert-butyldimethylsilyloxy-2-hydroxybutyric acid methyl ester (6)

After dissolving 2.96 g of a silyl-protected compound (5) (5.48 mmol) in methanol (100 mL), palladium black (200 mg) was added and the mixture was stirred for 3 hours under a hydrogen atmosphere. The catalyst was filtered off, the solvent was distilled off, and then the residue was dissolved in 100 mL of methylene chloride. A mixture of oxalyl chloride (952 µL, 11 mmol) and DMSO (1.17 mL, 16.4 mmol) prepared in methylene chloride at −78° C. was added thereto at −78° C., and the reaction mixture was stirred at −78° C. for 10 minutes and at −50° C. for one hour. After adding triethylamine (3 mL, 22 mmol) to the reaction mixture at −50° C., the temperature was raised to 0° C. and stirring was contained for 5 minutes. A saturated ammonium chloride aqueous solution was added to quench the reaction, extraction was performed with ether, and the organic layer was washed with 1N hydrochloric acid and a saturated sodium chloride aqueous solution and dried over magnesium sulfate. The residue obtained by distilling off the solvent was dissolved in 50 mL of acetone, and Jones reagent was added at 0° C. until the solution turned a brown color. 2-Propanol was added to quench the reaction, and extraction was performed with ether. Diazomethane was added to the organic layer for methyl esterification, and the solution was dried over magnesium sulfate. The solvent was distilled off, the obtained residue was dissolved in 100 mL of THF, and a THF solution (1 N, 11 mL) containing tetra-n-butylammonium fluoride was added. Ethyl acetate was added for extraction, and the organic layer was washed with a 5% citric acid aqueous solution. The organic layer was then dried over magnesium sulfate, and the lactone and diol mixture obtained by distilling off the solvent was dissolved in methanol, after which a catalytic amount of acidic resin (Amberlyst 15E) was added and the mixture was stirred for 16 hours. The catalyst was filtered off, the solvent was distilled off, the obtained residue was dissolved in DMF, and then t-butyldimethylsilyl chloride (828 mg, 5.5 mmol) and imidazole (748 mg, 11 mmol) were added and the mixture was stirred at room temperature for 3 hours. After adding methanol to quench the reaction and performing extraction with ether, the organic layer was washed with 1N hydrochloric acid and a saturated sodium chloride aqueous solution and dried over magnesium sulfate. The solvent was distilled off and the resulting residue was purified by silica gel column chromatography (ether/hexane=1/3) to obtain 1.25 g of the title compound (7 steps, 63%).

Oily: $[\alpha]_D$ +10.7° (c1.50, CHCl$_3$); $^1$H NMR (CDCl$_3$, 400 MHz); δ0.03 (s, 6H), 0.90 (s, 9H), 1.44 (s, 9H), 3.27 (d, 1H, J=4.0 Hz), 3.64 (dd, 1H, J=7.5 Hz, 9.5 Hz), 3.73 (dd, 1H, J=5.0, 9.5 Hz), 3.79 (s, 3H), 4.09 (m, 1H), 4.46 (m, 1H), 4.87 (d, 1H, J=9.0 Hz).

(2S,3R)-3-N-tert-Butoxycarbonylamino-4-tert-butyldimethylsilyloxy-2-(3-nitrobenzyl)oxybutyric acid methyl ester (7)

After adding sodium hydride (116 mg, 2.90 mmol) and tetra-n-butylammonium iodide (213 mg, 0.60 mmol) to 5 mL of a DMF solution containing a 2-OH compound (6) (700 mg, 1.93 mmol) at −20° C., 3-nitrobenzyl bromide (625 mg, 2.90 mmol) was further added thereto and the mixture was stirred at −20° C. for 30 minutes and at 0° C. for 30 minutes. A 5% citric acid aqueous solution was added to quench the reaction, extraction was performed with ether, and the organic layer was dried over magnesium sulfate. The solvent was distilled off and the resulting residue was purified by silica gel column chromatography (ether/hexane=1/3) to obtain 759 mg of the title compound (79%).

Oily: $[\alpha]_D$ −8.7° (c 1.94, CHCl$_3$); $^1$H NMR (CDCl$_3$, 400 MHz); δ0.03 (s, 3H), 0.06 (s, 3H), 0.86 (s, 9H), 1.40 (s, 9H), 3.57 (dd, 1H, J=9.5, 9.5 Hz), 3.69 (dd, 1H, J=5.0, 9.5 Hz), 3.77 (s, 3H), 4.18 (m, 1H), 4.39 (d, 1H, J=2.0 Hz), 4.50 (d, 1H, J=12.0 Hz), 4.86 (d, 1H, J=10.0 Hz), 4.88 (d, 1H, J=12.0 Hz), 7.53 (dd, 1H, J=8.0, 8.0 Hz), 7.71 (d, 1H, J=8.0 Hz), 8.16 (m, 1H), 8.22 (s, 1H).

(2S,3R)-2-[3-(3-N-Benzyloxycarbonylaminopropionylamino) benzyloxy]-3-N-tert-butoxycarbonylamino-4-tert-butyldimethylsilyloxybutyric acid methyl ester (8)

A catalytic amount of palladium carbon (10%) was added to 30 mL of a methanol solution containing a nitrobenzyl compound (7) (759 mg, 1.52 mmol), and the mixture was stirred for 3 hours under a hydrogen atmosphere. The catalyst was filtered off, and the filtrate was concentrated under reduced pressure. The residue was dissolved in 50 mL of methylene chloride, and then N-benzyloxycarbonyl-β-alanine (439 mg, 2 mmol) and 1-ethyl-3-(3-dimethylaminopropyl)carbodiimide hydrochloride (406 mg, 2 mmol) were added and the mixture was stirred at room temperature for 30 minutes. Ether and water were added for extraction, and the organic layer was washed with a 5% citric acid aqueous solution, water, a saturated sodium bicarbonate aqueous solution and water in that order. The organic layer was dried over magnesium sulfate, the solvent was distilled off and the resulting residue was purified by silica gel column chromatography (ether/hexane=3/1) to obtain 956 mg of the title compound (2 steps, 94%).

Oily: $[\alpha]_D$ −5.3° (c1.68, CHCl$_3$); $^1$H NMR (CDCl$_3$, 400 MHz); δ0.03 (s, 3H), 0.06 (s, 3H), 0.89 (s, 9H), 1.40 (s, 9H), 2.58 (m, 2H), 3.54 (m, 3H), 3.64 (dd, 1H, J=5.0, 9.5 Hz), 3.74 (s, 3H), 4.13 (m, 1H), 4.32 (br s, 1H), 4.36 (d, 1H, J=11.5 Hz), 4.69 (d, 1H, J=11.5 Hz), 4.98 (d, 1H, J=10.0 Hz), 5.08 (m, 2H), 5.66 (br s, 1H), 7.08 (d, 1H, J=7.0 Hz), 7.30 (m, 6H), 7.48 (m, 2H), 7.96 (s, 1H).

(2S,3S)-3-[3-(3-N-Benzyloxycarbonylaminopropionylamino) benzyloxy]-2-N-tert-butoxycarbonyl-aspartic acid δ-methyl ester (9)

A catalytic amount of DL-camphorsulfonic acid was added to 10 mL of a methanol solution containing compound (8) (777 mg, 1.15 mmol) and the mixture was stirred for 5 hours. Ether and water were added for extraction, and the organic layer was dried over magnesium sulfate. The residue obtained by distilling off the solvent was dissolved in 5 mL of acetone, and Jones reagent was added at 0° C. until the solution brownness no longer disappeared. 2-Propanol was added to quench the reaction, and extraction was performed with ether. After extraction into an aqueous layer with a saturated sodium bicarbonate aqueous solution, the aqueous layer was adjusted to pH 2 with 2N hydrochloric acid, and extraction was again performed into an organic layer with ethyl acetate. The organic layer was dried over magnesium sulfate, and the residue obtained by distilling off the solvent was purified by silica gel column chromatography (methanol/chloroform=1/19) to obtain 210 mg of the title compound (2 steps, 32%).

Oily: $[\alpha]_D$ −52.5° (c0.46, CHCl$_3$); $^1$H NMR (CDCl$_3$, 400 MHz); δ1.40 (s, 9H), 2.53 (m, 2H), 3.48 (m, 2H), 3.77 (s, 3H), 4.29 (d, 1H, J=12.5 Hz), 4.45 (d, 1H, J=2.5 Hz), 4.81 (m, 2H), 5.07 (s, 2H), 5.48 (d, 1H, J=9.5 Hz), 5.83 (m, 1H), 6.96 (d, 1H, J=7.0 Hz), 7.17-7.36 (m, 8H), 8.44 (br s, 1H).

(2S,3S)-3-[3-(3-aminopropionylamino)benzyloxy]aspartic acid (AA-TBOA)

After adding 1.5 mL of a 1N sodium hydroxide aqueous solution to 1 mL of a methanol solution of Compound (9) (190 mg, 0.33 mmol), the mixture was stirred while cooling on ice for one hour and at room temperature for 16 hours. After adding 1 mL of 2N hydrochloric acid, extraction was performed with ethyl acetate, and the organic layer was washed with a saturated sodium chloride aqueous solution and dried over magnesium sulfate. The residue obtained by distilling off the solvent was dissolved in methanol (5 mL), after which catalytic amounts of hydrochloric acid and palladium black were added and the mixture was stirred under a hydrogen atmosphere for 3 hours. The catalyst was filtered off, the residue obtained by concentrating the filtrate was dissolved in 2 mL of methylene chloride, 1 mL of trifluoroacetic acid was added and the mixture was stirred for 15 minutes. The solvent was distilled off, the residue was subjected to Dowex 50×100 column chromatography and washed with water, and then elution was performed with 1N ammonia water. Lyophilization was repeated to obtain the title compound (97 mg, 91%).

Amorphous: $[\alpha]_D$ −25.0° (c 0.88, $H_2O$); $^1H$ NMR ($D_2O$, 400 MHz); δ2.74 (t, 2H, J=6.5 Hz), 3.18 (t, 2H, J=6.5 Hz), 3.69 (s, 1H), 4.24 (s, 1H), 4.42 (d, 1H, J=12.0 Hz), 4.71 (d, 1H, J=12.0 Hz), 7.22 (d, 1H, J=7.0 Hz), 7.36 (d, 1H, J=7.0 Hz), 7.41 (dd, 1H, J=7.0 Hz, 7.5 Hz), 7.50 (d, 1H, J=7.5 Hz).

(2S,3S)-3-[3-(3-N-biotinylaminopropionylamino)benzyloxy]-2-N-tert-butoxycarbonyl-aspartic acid δ-methyl ester (10)

A catalytic amount of palladium carbon (10%) was added to 5 mL of a methanol solution containing compound (8) (107 mg, 0.20 mmol), and the mixture was stirred for 3 hours under a hydrogen atmosphere. The catalyst was filtered off, the residue obtained by concentrating the filtrate was dissolved in 2 mL of methylene chloride, and then biotin, pentafluorophenyl ester (91 mg, 0.22 mmol) and triethylamine (30 μL, 0.22 mmol) were added and the mixture was stirred at room temperature for 30 minutes. The reaction solution was diluted with ether, and washed with 1N hydrochloric acid and water. The organic layer was dried over magnesium sulfate.

The residue obtained by distilling off the solvent was purified by silica gel column chromatography (methanol/chloroform=1/10) to obtain 55 mg of the title compound (2 steps, 46%).

Oily: $[\alpha]_D$ −26.8° (c 0.58, MeOH) $^1H$ NMR (CDCl₃, 400 MHz); δ1.40 (s, 9H), 1.5-1.8 (m, 6H), 2.26 (m, 2H), 2.66 (m, 2H), 2.77 (m, 3H), 2.89 (dd, 1H, J=4.5, 13.0 Hz), 3.13 (m, 1H), 3.46 (m, 1H), 3.68 (m, 1H), 3.75 (s, 3H), 4.34 (m, 1H), 4.42 (d, 1H, J=13.0 Hz), 4.44 (d, 1H, J=2.0 Hz), 4.51 (m, 1H), 4.80 (dd, 1H, J=2.0, 9.5 Hz), 4.91 (d, 1H, J=13.0 Hz), 5.49 (d, 1H, J=9.5 Hz), 6.52 (m, 1H), 6.61 (s, 1H), 6.66 (s, 1H), 6.86 (d, 1H, J=7.5 Hz), 7.02 (s, 1H), 8.04 (d, 1H, J=8.0 Hz), 8.87 (s, 1H).

(2S,3S)-3-[3-(3-N-biotinylaminopropionylamino)benzyloxy] aspartic acid (Bio-AA-TBOA)

After adding 66 μL of a 1N sodium hydroxide aqueous solution to 1 mL of a methanol solution containing compound (10) (13 mg, 0.22 mmol), the mixture was stirred at room temperature for 18 hours. The reaction solution was adjusted to pH 1 with 2N hydrochloric acid, and extraction was performed with ethyl acetate. The organic layer was dried over magnesium sulfate, and the residue obtained by distilling off the solvent was dissolved in 1 mL of chloroform prior to adding 1 mL of trifluoroacetic acid and stirring for 15 minutes. The solvent was distilled off, the residue was subjected to Dowex 50×100 column chromatography and washed with water, and then elution was performed with 1N ammonia water. Lyophilization was repeated to obtain 7.9 mg of the title compound (72%).

Amorphous: $[\alpha]_D$ +6.1° (c 0.32, 50% DMSO-$H_2O$); $^1H$ NMR ($D_2O$, 400 MHz); δ1.15 (m, 2H), 1.32 (m, 1H), 1.45 (m, 3H), 2.53 (dd, 1H, J=4.0, 12.5 Hz), 2.54 (m, 2H), 2.66 (dd, 1H, J=5.0, 12.5 Hz), 2.81 (m, 1H), 3.44 (m, 2H), 3.48 (d, 1H, J=4.5 Hz), 3.90 (dd, 1H, J=1.0, 2.0 Hz), 3.94 (dd, 1H, J=4.5, 8.0 Hz), 4.24 (m, 2H), 4.37 (d, 1H, J=12 Hz), 4.60 (d, 1H, J=12 Hz), 7.09 (d, 1H, J=7.5 Hz), 7.22 (s, 1H), 7.29 (dd, 1H, J=7.5, 7.5 Hz), 7.38 (d, 1H, J=7.5 Hz).

(2S,3R)-2-[3-(3-N-propionylaminopropionylamino)benzyloxy]-3-N-tert-butoxy-carbonylamino-4-tert-butyldimethyl-silyloxybutyric acid methyl ester (11)

A catalytic amount of palladium carbon (10%) was added to 10 mL of a methanol solution containing compound (8) (110 mg, 0.16 mmol), and the mixture was stirred for 3 hours under a hydrogen atmosphere. The catalyst was filtered off, and the filtrate was concentrated under reduced pressure. The residue was dissolved in 10 mL of methylene chloride, and then triethylamine (45 μL, 0.32 mmol) and propionyl chloride (16 μL, 0.19 mmol) were added while cooling on ice and the mixture was stirred for 15 minutes. Ether and water were added for extraction, and the organic layer was washed with a saturated sodium bicarbonate aqueous solution, a 5% citric acid aqueous solution and water in that order. The organic layer was dried over magnesium sulfate, the solvent was distilled off and the resulting residue was purified by silica gel column chromatography (ether/hexane=3/1) to obtain 75 mg of the title compound (2 steps, 79%).

Oily: $^1H$ NMR (CDCl₃, 400 MHz); δ0.03 (s, 3H), 0.05 (s, 3H), 0.87 (s, 9H), 1.12 (t, 3H, J=7.5 Hz), 1.40 (s, 9H), 2.19 (q, 2H, J=7.5 Hz), 2.62 (t, 2H, J=5.5 Hz), 3.58 (m, 4H), 3.75 (s, 3H), 4.11 (m, 1H), 4.32 (d, 1H, J=1.5 Hz), 4.38 (d, 1H, J=11.5 Hz), 4.73 (d, 1H, J=11.5 Hz), 4.98 (d, 1 H, J=9.5 Hz), 6.44 (t, 1H, J=5.5 Hz), 7.09 (d, 1H, J=7.5 Hz), 7.28 (m, 1H), 7.51 (m, 2H), 8.38 (s, 1H).

(2S,3S)-3-[3-(3-N-propionylaminopropionylamino)benzyloxy]aspartic acid (Pr-AA-TBOA)

A catalytic amount of DL-camphorsulfonic acid was added to 10 mL of a methanol solution containing compound (11) (57 mg, 0.096 mmol) and the mixture was stirred for 3 hours. Ether and water were added for extraction, and the organic layer was dried over magnesium sulfate. The solvent was distilled off, the resulting residue was dissolved in 5 mL of acetone, and Jones reagent was added at 0° C. until the solution brownness no longer disappeared. 2-Propanol was added to quench the reaction, and extraction was performed with ether. After extraction into an aqueous layer with a saturated sodium bicarbonate aqueous solution, the aqueous layer was adjusted to pH 2 with 2N hydrochloric acid, and extraction was again performed into an organic layer with ethyl acetate. The organic layer was dried over magnesium sulfate and the residue obtained by distilling off the solvent was dissolved in 1 mL of methanol, after which 1 mL of a 1N sodium hydroxide aqueous solution was added and the mixture was stirred at room temperature for 18 hours. The reaction solution was adjusted to pH 1 with 2N hydrochloric acid, and extraction was performed with ethyl acetate. The organic layer was dried over magnesium sulfate, and the residue obtained by distilling off the solvent was dissolved in 1 mL of chloroform prior to adding 1 mL of trifluoroacetic acid and stirring for 15 minutes. The solvent was distilled off, the residue was subjected to Dowex 50×100 column chromatography and washed with water, and then elution was performed with 1N ammonia water. Lyophilization was repeated to obtain 14 mg of the title compound (5 steps, 39%).

Amorphous: $[\alpha]_D$ −17.3° (c 0.71, $H_2O$); $^1$H NMR ($D_2O$, 400 MHz); δ1.11 (t, 3H, J=7.5 Hz), 2.27 (q, 2H, J=7.5 Hz), 2.66 (t, 2H, J=6.5 Hz), 3.57 (t, 2H, J=6.5 Hz), 3.68 (s, 1H), 4.24 (s, 1H), 4.44 (d, 1H, J=12.0 Hz), 4.72 (d, 1H, J=12.0 Hz), 7.24 (d, 1H, J=7.5 Hz), 7.32 (s, 1H), 7.43 (t, 1H, J=7.5 Hz), 7.51 (d, 1H, J=7.5 Hz).

As compounds without β-alanine, there were also synthesized A-TBOA, Bio-A-TBOA, Pr-A-TBOA, Piv-A-TBOA, PhAcA-TBOA, cHexcA-TBOA, BzA-TBOA, o-MeO-BzA-TBOA, m-MeO-BzA-TBOA, p-MeO-BzA-TBOA, diMeO-BzA-TBOA, tBu-BzA-TBOA, Ph-BzA-TBOA, CN-BzA-TBOA, $NO_2$-BzA-TBOA, F-BzA-TBOA, $OCF_3$-BzA-TBOA, $CF_3$-BzA-TBOA, OHex-BzA-TBOA and Hep-BzA-TBOA, by the same method according to Scheme 3.

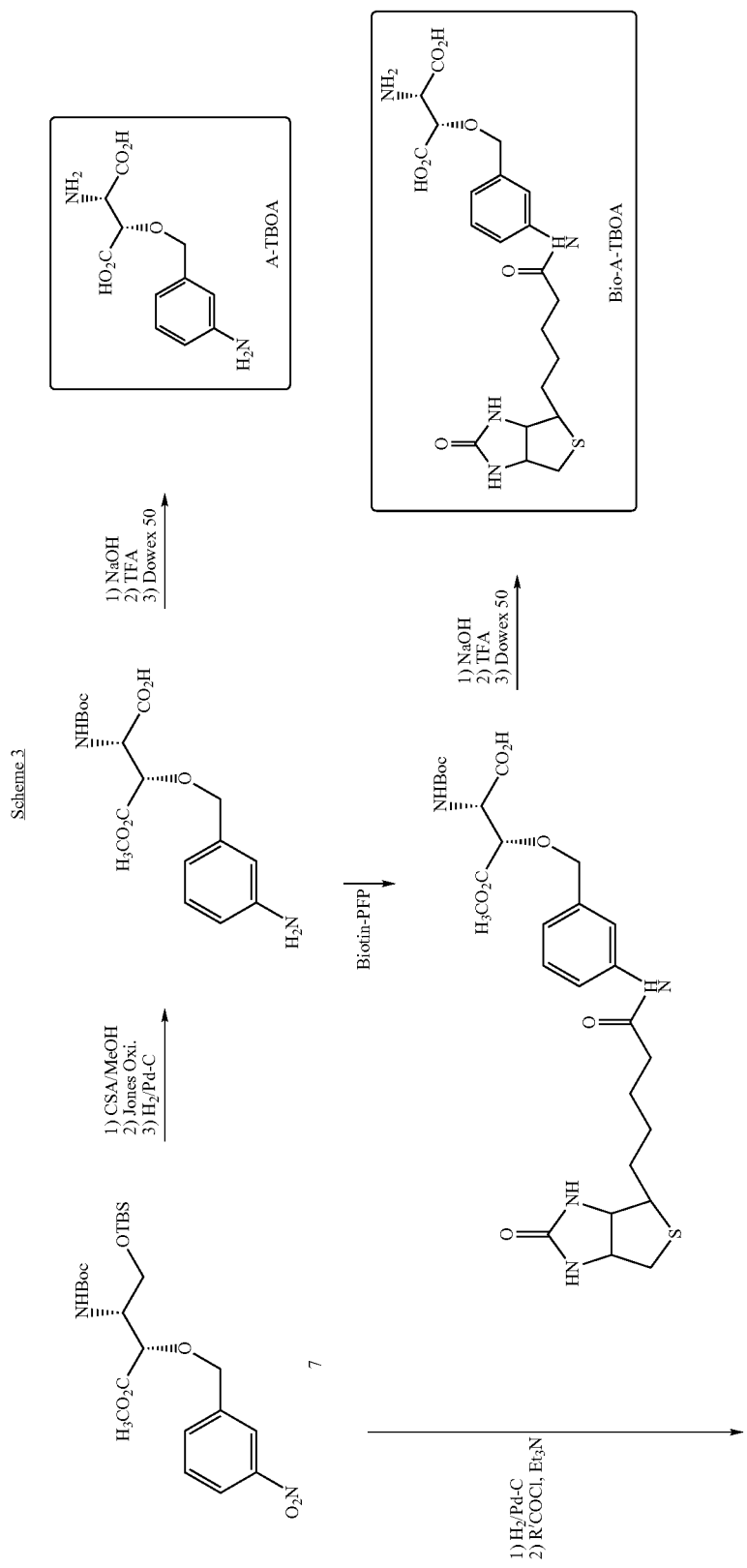

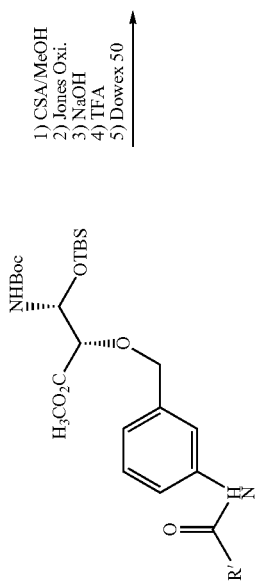
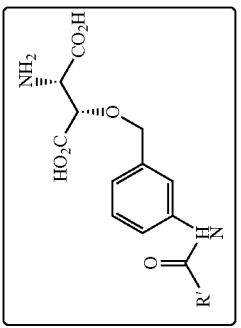
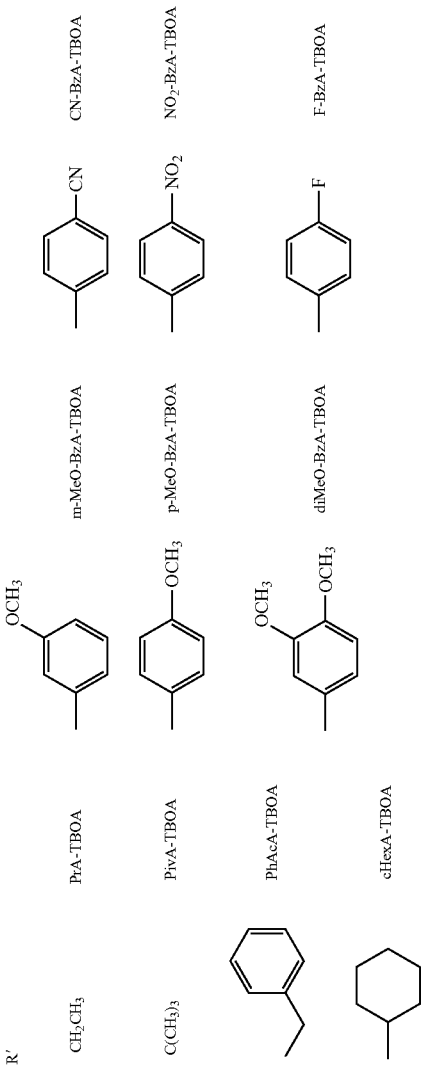

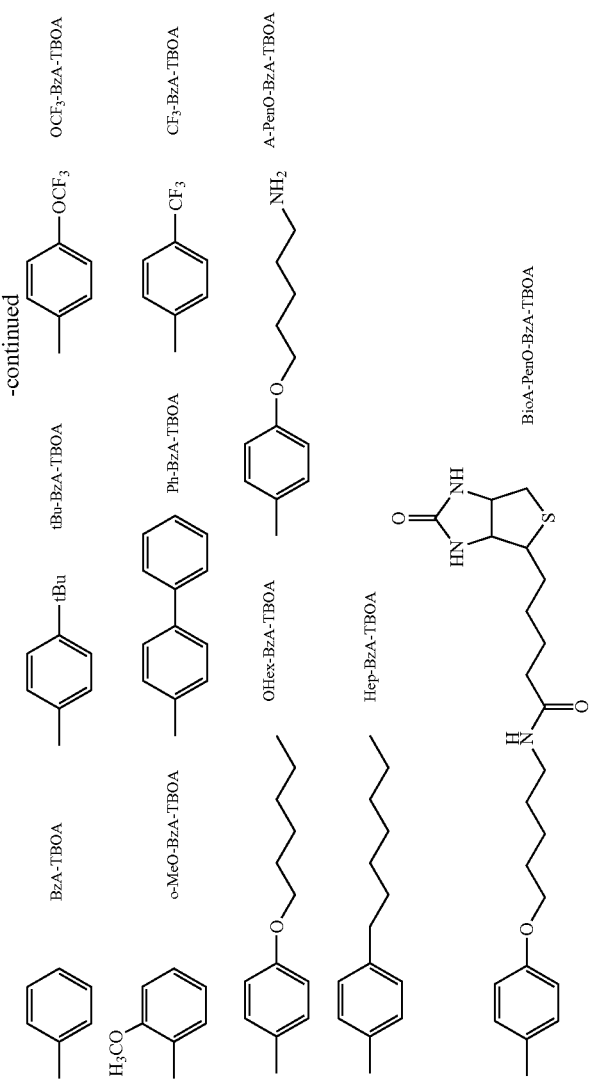

(2S,3S)-3-(3-aminobenzyloxy)aspartic acid (A-TBOA)

Amorphous: ¹H NMR (D₂O, 400 MHz); δ3.86 (d, 1H, J=2.0 Hz), 4.19 (d, 1H, J=2.0 Hz), 4.26 (d, 1H, J=11.6 Hz), 4.52 (d, 1H, J=11.6 Hz), 6.70 (m, 3H), 7.10 (t, 1H, J=7.6 Hz).

(2S,3S)-3-[3-(N-biotinylamino)benzyloxy]aspartic acid (Bio-A-TBOA)

Amorphous: [α]$_D$ +31.1° (c 0.35, H₂O); δ1.53 (m, 2H), 1.68 (m, 1H), 1.79 (m, 3H), 2.49 (t, 2H, J=7.8 Hz), 2.82 (d, 1H, J=13.0 Hz), 3.04 (dd, 1H, J=5.0, 13.0 Hz), 3.40 (m, 1H), 3.70 (s, 1H), 4.26 (s, 1H), 4.44 (d, 1H, J=12.0 Hz), 4.47 (dd, 1H, J=4.5, 8.0 Hz), 4.67 (dd, 1H, J=5.0, 7.5 Hz), 4.73 (d, 1H, J=12.0 Hz), 7.25 (d, 1H, J=7.5 Hz), 7.32 (s, 1H), 7.44 (t, 1H, J=7.5 Hz), 7.53 (d, 1H, J=7.5 Hz).

(2S,3S)-3-[3-(N-propionylamino)benzyloxy]aspartic acid (Pr-A-TBOA)

Amorphous: ¹H NMR (D₂O, 400 MHz); δ1.07 (t, 3H, J=7.5 Hz), 2.30 (q, 2H, J=7.5 Hz), 3.70 (s, 1H), 4.14 (s, 1H), 4.31 (d, 1H, J=12.0 Hz), 4.58 (d, 1H, J=12.0 Hz), 7.08 (d, 1H, J=7.5 Hz), 7.13 (s, 1H), 7.28 (d, 1H, J=7.5 Hz), 7.34 (d, 1H, J=8.0 Hz).

(2S,3S)-3-[3-(N-pivaroylamino)benzyloxy]aspartic acid (Piv-A-TBOA)

Amorphous: [α]$_D$ −27.7° (c 0.31, H₂O); ¹H NMR (D₂O, 400 MHz); δ1.20 (s, 9H), 3.86 (dd, 1H, J=2.0, 2.5 Hz), 4.20 (dd, 1H, J=2.0, 2.5 Hz), 4.34 (d, 1H, J=12 Hz), 4.57 (d, 1H, J=12 Hz), 7.10 (d, 1H, J=7.0 Hz), 7.17 (s, 1H), 7.25 (m, 2H)

(2S,3S)-3-[3-(N-phenylacetylamino)benzyloxy]aspartic acid (PhAcA-TBOA)

¹H-NMR (DMSO-d₆, D₂O) δ: 3.61 (s, 2H), 3.89 (d, 1H, J=8.5 Hz), 4.16 (d, 1H, J=8.5 Hz), 4.43 (d, 1H, J=11.0 Hz), 4.76 (d, 1H, J=11.0 Hz), 7.14 (d, 1H, J=7.0 Hz), 7.20-7.35 (m, 6H), 7.53 (d, 1H, J=7.0 Hz), 7.55 (s, 1H).

(2S,3S)-3-[3-(N-cyclohexylcarbonylamino)benzyloxy]aspartic acid (cHexcA-TBOA)

¹H-NMR (DMSO-d₆, D₂O) δ: 1.10-1.42 (m, 6H), 1.73 (m, 4H), 2.29 (m, 1H), 4.27 (d, 1H, J=3.5 Hz), 4.46 (d, 1H, J=12.0 Hz), 4.49 (d, 1H, J=3.5 Hz), 4.72 (d, 1H, J=12.0 Hz), 7.03 (d, 1H, J=7.5 Hz), 7.26 (t, 1H, J=7.5 Hz), 7.46 (d, 1H, J=8.0 Hz), 7.55 (s, 1H).

(2S,3S)-3-[3-(N-benzoylamino)benzyloxy]aspartic acid (BzA-TBOA)

¹H-NMR (CD₃OD) δ: 4.46 (d, 1H, J=11.5 Hz), 4.59 (d, 1H, J=2.5 Hz), 4.72 (d, 1H, J=2.5 Hz), 4.82 (d, 1H, J=11.5 Hz), 7.14 (d, 1H, J=7.5 Hz), 7.34 (t, 1H, J=7.5 Hz), 7.50 (m, 2H), 7.57 (m, 1H), 7.63 (s, 1H), 7.67 (d, 1H, J=7.5 Hz), 7.93 (m, 2H).

(2S,3S)-3-[3-[N-(2-methoxybenzoyl)amino]benzyloxy]aspartic acid (o-MeO-BzA-TBOA)

¹H-NMR (DMSO-d₆, D₂O) δ: 3.86 (3H, s), 4.06 (d, 1H, J=4.0 Hz), 4.42 (d, 1H, J=4.0 Hz), 4.48 (d, 1H, J=11.5 Hz), 4.72 (d, 1H, J=11.5 Hz), 7.05 (t, 1H, J=7.5 Hz), 7.19 (d, 1H, J=7.5 Hz), 7.14 (d, 1H, J=7.5 Hz), 7.31 (t, 1H, J=7.5 Hz), 7.49 (dt, 1H, J=1.5, 8.0 Hz), 7.59 (s, 1H), 7.60 (d, 1H, J=7.5 Hz), 7.65 (dd, 1H, J=1.5, 7.5 Hz).

(2S,3S)-3-[3-[N-(3-methoxybenzoyl)amino]benzyloxy]aspartic acid (m-MeO-BzA-TBOA)

¹H-NMR (DMSO-d₆, D₂O) δ: 3.84 (s, 3H), 4.15 (d, 1H, J=4.5 Hz), 4.39 (d, 1H, J=4.5 Hz), 4.50 (d, 1H, J=9.5 Hz), 4.80 (d, 1H, J=9.5 Hz), 7.16 (m, 2H), 7.33 (t, 1H, J=6.5 Hz), 7.44 t, 1H, J=6.5 Hz), 7.47 (m, 1H), 7.53 (d, 1H, J=6.5 Hz), 7.67 (d, 1H, J=7.0 Hz), 7.74 (s, 1H).

(2S,3S)-3-[3-[N-(4-methoxybenzoyl)amino]benzyloxy]aspartic acid (p-MeO-BzA-TBOA)

¹H-NMR (DMSO-d₆, D₂O) δ:3.82 (s, 3H), 3.95 (d, 1H, J=7.5 Hz), 4.23 (d, 1H, J=7.5 Hz), 4.48 (d, 1H, J=11.0 Hz), 4.80 (d, 1H, J=11.0 Hz), 7.04 (d, 2H, J=9.0 Hz), 7.18 (d, 1H, J=7.5 Hz), 7.30 (t, 1H, J=7.5 Hz), 7.66 (d, 1H, J=7.5 Hz), 7.72 (s, 1H), 7.94 (d, 2H, J=9.0 Hz).

(2S,3S)-3-[3-[N-(3,4-dimethoxybenzoyl)amino]benzyloxy]aspartic acid (diMeO-BzA-TBOA)

¹H-NMR (DMSO-d₆, D₂O) δ: 3.79 (s, 6H), 4.14 (d, 1H, J=4.5 Hz), 4.41 (d, 1H, J=4.5 Hz), 4.48 (d, 1H, J=9.5 Hz), 4.71 (d, 1H, J=9.5 Hz), 7.04 (d, 1H, J=8.5 Hz), 7.10 (d, 1H, J=7.5 Hz), 7.31 (t, 1H, J=6.5 Hz), 7.46 (d, 1H, J=2.0 Hz), 7.55 (dd, 1H, J=2.5, 8.5 Hz), 7.58 (d, 2H, J=8.5 Hz).

(2S,3S)-3-[3-[N-(4-tert-butylbenzoyl)amino]benzyloxy]aspartic acid (tBu-BzA-TBOA)

¹H-NMR (DMSO-d₆, D₂O) δ: 1.33 (s, 9H), 4.05 (s, 1H), 7.08 (d, 1H, J=7.0 Hz), 7.32 (t, 1H, J=7.5 Hz), 7.48 (s, 2H), 7.50 (d, 2H, J=7.5 Hz), 7.74 (d, 2H, J=7.5 Hz).

(2S,3S)-3-[3-[N-(4-phenylbenzoyl)amino]benzyloxy]aspartic acid (Ph-BzA-TBOA)

¹H-NMR (DMSO-d₆, D₂O) δ: 3.92 (d, 1H, J=3.5 Hz), 4.38 (d, 1H, J=3.5 Hz), 4.48 (d, 1H, J=12.0 Hz), 4.71 (d, 1H, J=12.0 Hz), 7.13 (d, 1H, J=8.0 Hz), 7.33 (t, 1H, J=8.0 Hz), 7.39 (t, 1H, J=7.5 Hz), 7.48 (t, 2H, J=7.5 Hz), 7.64 (m, 2H), 7.50 (d, 2H, J=8.0 Hz), 7.78 (d, 2H, J=8.0 Hz), 7.98 (d, 2H, J=8.0 Hz)

(2S,3S)-3-[3-[N-(4-cyanobenzoyl)amino]benzyloxy]aspartic acid (CN-BzA-TBOA)

¹H-NMR (DMSO-d₆, D₂O) δ: 4.30 (d, 1H, J=3.5 Hz), 4.52 (d, 1H, J=3.5 Hz), 4.54 (d, 1H, J=12.0 Hz), 4.79 (d, 1H, J=12.0 Hz), 7.16 (d, 1H, J=7.5 Hz), 7.37 (t, 1H, J=7.5 Hz), 7.64 (d, 1H, J=8.0 Hz), 7.71 (s, 1H), 7.98 (d, 2H, J=8.5 Hz), 8.07 (d, 2H, J=8.5 Hz).

(2S,3S)-3-[3-[N-(4-nitrobenzoyl)amino]benzyloxy]aspartic acid (NO₂-BzA-TBOA)

¹H-NMR (DMSO-d₆, D₂O) δ: 4.28 (d, 1H, J=3.5 Hz), 4.50 (d, 1H, J=3.5 Hz), 4.52 (d, 1H, J=11.5 Hz), 4.76 (d, 1H, J=11.5 Hz), 7.14 (d, 1H, J=8.0 Hz), 7.36 (t, 1H, J=8.0 Hz), 7.62 (d, 1H, J=8.0 Hz), 7.69 (s, 1H), 8.10 (d, 2H, J=8.5 Hz), 8.32 (d, 2H, J=8.5 Hz).

(2S,3S)-3-[3-[N-(4-fluorobenzoyl)amino]benzyloxy]aspartic acid (F-BzA-TBOA)

¹H-NMR (DMSO-d₆, D₂O) δ: 4.30 (d, 1H, J=3.5 Hz), 4.52 (d, 1H, J=3.5 Hz), 4.53 (d, 1H, J=11.5 Hz), 4.77 (d, 1H, J=11.5 Hz), 7.12 (d, 1H, J=7.5 Hz), 7.33 (m, 3H), 7.63 (d, 1H, J=8.0 Hz), 7.70 (s, 1H), 7.99 (m, 2H).

(2S,3S)-3-[3-[N-(4-trifluoromethoxybenzoyl)amino]benzyloxy]aspartic acid (OCF₃-BzA-TBOA)

¹H-NMR (DMSO-d₆, D₂O) δ: 4.25 (d, 1H, J=3.5 Hz), 4.48 (d, 1H, J=3.5 Hz), 4.50 (d, 1H, J=12.0 Hz), 4.65 (d, 1H, J=12.0 Hz), 7.14 (d, 1H, J=8.0 Hz), 7.32 (t, 1H, J=8.0 Hz), 7.46 (d, 2H, J=8.5 Hz), 7.59 (s, 1H), 7.61 (d, 1H, J=8.0 Hz), 7.99 (d, 2H, J=8.5 Hz).

(2S,3S)-3-[3-[N-(4-trifluoromethylbenzoyl)amino]benzyloxy]aspartic acid (CF₃-BzA-TBOA)

¹H-NMR (DMSO-d₆, D₂O) δ: 4.28 (d, 1H, J=3.5 Hz), 4.51 (d, 1H, J=3.5 Hz), 4.53 (d, 1H, J=12.0 Hz), 4.77 (d, 1H, J=12.0 Hz), 7.14 (d, 1H, J=7.5 Hz), 7.36 (t, 1H, J=7.5 Hz), 7.63 (d, 1H, J=8.0 Hz), 7.70 (s, 1H), 7.87 (d, 2H, J=8.5 Hz), 8.08 (d, 2H, J=8.5 Hz).

(2S,3S)-3-[3-[N-(4-n-hexyloxybenzoyl)amino]benzyloxy] aspartic acid (OHex-BzA-TBOA)

$^1$H-NMR (DMSO-d$_6$, D$_2$O) δ: 0.81 (t, 3H, J=7.0 Hz), 1.24 (m, 6H), 1.35 (m, 2H), 3.92 (d, 1H, J=4.0 Hz), 3.99 (t, 2H, J=6.5 Hz), 4.38 (d, 1H, J=4.0 Hz), 4.46 (d, 1H, J=11.5 Hz), 4.68 (d, 1H, J=11.5 Hz), 6.98 (d, 2H, J=9.0 Hz), 7.09 (d, 1H, d, J=7.5 Hz), 7.30 (t, 1H, J=7.5 Hz), 7.57 (s, 1H), 7.58 (d, 1H, J=7.5 Hz), 7.84 (d, 2H, J=9.0 Hz).

(2S,3S)-3-[3-[N-(4-n-heptylbenzoyl)amino]benzyloxy]aspartic acid (Hep-BzA-TBOA)

$^1$H-NMR (DMSO-d$_6$, D$_2$O) δ: 0.83 (t, 3H, J=6.5 Hz), 1.24 (m, 8H), 1.56 (m, 2H), 2.62 (t, 2H, J=7.5 Hz), 3.81 (d, 1H, J=6.5 Hz), 4.28 (d, 1H, J=6.5 Hz), 4.48 (d, 1H, J=11.0 Hz), 4.75 (d, 1H, J=11.0 Hz), 7.17 (d, 1H, J=7.5 Hz), 7.30 (m, 3H), 7.68 (m, 2H), 7.85 (d, 2H, J=7.5 Hz).

A para-substituted form (p-Pr-A-TBOA) was also synthesized by the same method.

(2S,3S)-3-[4-(N-propionylamino)benzyloxy]aspartic acid (p-Pr-A-TBOA)

Amorphous: $^1$H NMR (50% D$_2$O/DMSO-d$_6$, 400 MHz); δ1.03 (t, 3H, J=7.5 Hz), 2.27 (q, 2H, J=7.5 Hz), 4.20 (s, 1H), 4.43 (d, 1H, J=12.0 Hz), 4.60 (s, 1H), 4.66 (d, 1H, J=12.0 Hz), 7.22 (d, 2H, J=7.0 Hz), 7.39 (m, 2H).

(2S,3S)-3-[3-(N-(4-(5-aminopentyloxy)benzoyl)amino) benzyloxy]aspartic acid (A-PenO-BzA-TBOA)

$^1$H-NMR (D$_2$O) δ: 1.36 (tt, 2H, J=7.5 Hz), 1.58 (tt, 2H, J=7.5 Hz), 1.66 (tt, 2H, J=7.5 Hz), 2.86 (t, 2H, J=7.5 Hz), 3.94 (t, 2H, J=6.0 Hz), 4.30 (s, 1H), 4.44 (d, 1H, J=12.0 Hz), 4.52 (s, 1H), 4.68 (d, 1H, J=12.0 Hz), 6.89 (d, 2H, J=7.5 Hz), 7.08 (d, 1H, J=7.0 Hz), 7.31 (m, 3H), 7.66 (d, 2H, J=7.5 Hz).

(2S,3S)-3-[3-(N-(4-(5-biotynylaminopentyloxy)benzoyl) amino)benzyloxy] aspartic acid (BioA-PenO-BzA-TBOA)

$^1$H-NMR (DMSO-d$_6$, D$_2$O) δ: 1.20-1.65 (m, 12H), 1.71 (m, 2H), 2.04 (t, 2H J=7.0 Hz), 2.56 (d, 1H, J=13.0 Hz), 2.78 (dd, 1H, J=4.5, 13.0 Hz), 3.05 (m, 3H), 4.01 (t, 2H, J=5.5 Hz), 4.13 (m, 1H), 4.32 (m, 1H), 4.48 (d, 1H, J=11.5 Hz), 4.71 (d, 1H, J=11.5 Hz), 7.01 (d, 2H, J=8.0 Hz), 7.13 (d, 1H, J=7.0 Hz), 7.30 (t, 1H, J=7.5 Hz), 7.64 (m, 2H), 7.89 (d, 2H, J=8.0 Hz).

Activity Evaluation

A known method (Shimamoto, K. et al., Mol. Pharmacol. 53, 195-201, 1998; Bioorg. Med. Chem. Lett. 10, 2407-2410, 2000) was used to measure the inhibitory effect on uptake of [$^{14}$C]glutamate by human EAAT2 and EAAT3 stably expressed on MDCK (Madin-Darby Canine Kidney) cells or transiently expressed on COS-1 cells. The glutamate uptake activity was measured by adding 1 μM of L-[$^{14}$C] glutamate and a prescribed concentration of sample, incubating for 12 minutes and then lysating the cells, and using a liquid scintillator to determine the radioactivity uptake. The uptake was expressed as a percentage, with 100% being the uptake with no compound (buffer alone) and 0% being the uptake with a sodium-free solution. The IC$_{50}$ values are shown in Table 1.

TABLE 1

| | EAAT2 | EAAT3 |
|---|---|---|
| TBOA | 1.4 ± 0.12 μM | 1.3 ± 0.11 μM |
| A-TBOA | 2.1 ± 0.1 μM | 7.9 ± 0.76 μM |
| AA-TBOA | 13 ± 1.1 μM | 13 ± 1.1 μM |
| Pr-A-TBOA | 2.0 ± 0.21 μM | 7.9 ± 0.46 μM |
| Piv-A-TBOA | 1.0 ± 0.13 μM | 4.1 ± 0.67 μM |
| Pr-AA-TBOA | 6.0 ± 1.4 μM | 7.6 ± 0.45 μM |

TABLE 1-continued

| | EAAT2 | EAAT3 |
|---|---|---|
| BioA-TBOA | 38 ± 13 μM | 25 ± 2.4 μM |
| Bio-AA-TBOA | 6.3 ± 0.39 μM | 10 ± 0.93 μM |
| PhAcA-TBOA | 143 ± 7.9 nM | 529 ± 32 nM |
| CHexA-TBOA | 244 ± 12 nM | 288 ± 8.0 nM |
| BzA-TBOA | 55 ± 5.0 nM | 726 ± 98 nM |
| cHexcA-TBOA | 145 ± 2.2 nM | 1000 ± 42 nM |
| m-MeO-BzA-TBOA | 37 ± 2.5 nM | 356 ± 12 nM |
| p-MeO-BzA-TBOA | 12 ± 0.5 nM | 266 ± 20 nM |
| DiMeO-BzA-TBOA | 49 ± 3.8 nM | 917 ± 30 nM |
| TBu-BzA-TBOA | 25 ± 0.5 nM | 182 ± 11 nM |
| Ph-BzA-TBOA | 21 ± 2.2 nM | 34 ± 19 nM |
| TBu-BzA-TBOA | 36 ± 2.9 nM | 1400 ± 99 nM |
| NO$_2$-BzA-TBOA | 14 ± 1.4 nM | 278 ± 32 nM |
| F-BzA-TBOA | 22 ± 2.7 nM | 473 ± 13 nM |
| OCF$_3$-BzA-TBOA | 7.0 ± 0.5 nM | 128 ± 12 nM |
| CF$_3$-BzA-TBOA | 1.9 ± 0.10 nM | 28 ± 1.8 nM |
| OHex-BzA-TBOA | 1.2 ± 0.04 nM | 18 ± 1.6 nM |
| p-Pr-A-TBOA | 111 ± 25 μM* | 295 ± 118 μM* |
| A-PenO-BzA-TBOA | 7.3 ± 1.1 μM | 2.2 ± 0.20 μM |
| BioA-PenO-BzA-TBOA | 2.2 ± 0.52 μM | 1.1 ± 0.06 μM |

The "*" indicates results obtained using COS-1 cells, and the other results were obtained using MDCK cells.

The results show that the inhibitory effect of the compounds of the invention on uptake of [$^{14}$C]glutamate by human EAAT2 and EAAT3 is at least comparable to, or in some compounds, remarkably higher than that of TBOA. Besides, it will be appreciated that the inhibitory effect of some compounds in table 1 is selective to EAAT2 over EAAT3.

Preparation of Affinity Column Ligand

Preparatiom Example 1

A prescribed amount of CNBr-activated Sepharose 4B (Amersham Biosciences) is weighed on a glass filter. Washing and swelling are repeated using 1 mM HCl. A compound of the invention (ligand) is solubilized in a coupling buffer (e.g., 0.1 M NaHCO$_3$ containing 0.5 M NaCl, pH 8.3). The ligand solution is mixed with the gel suspension for two hours at an ambient temperature or overnight at 4° C. Subsequently, the gell is introduced into a blocking agent such as 1 M ethanolamine or 0.2 M glycine, pH 8.0. The gel is washed with the coupling buffer and acetate buffer (0.5 M NaCl, 0.1 M AcOH, pH 4) in that order to remove excess ligand and blocking agent. The gel is stored at 4-8%.

Preparation Example 2

A prescribed amount of ECH Sepharose 4B (Amersham Biosciences) is weighed on a glass filter and washed with 0.5 M NaCl. A compound of the invention (ligand) is solubilized in water, which is then adjusted at pH 4.5. An aqueous solution of carbodiimide is prepared and the pH of the solution is adjusted at pH 4.5. The swollen gel, the ligand solution and the carbodiimide solution are mixed to allow to react at an ambient temperature overnight. Excess ligand, urea derivatives and remaining ligand are removed by washing. The gel is stored at 4-8° C.

Preparation Example 3

Immobilized avidin or streptavidin slury is poured into a column. The packed column is equilibrated with 5 column volumes of binding buffer (e.g., PBS). A biotinylated compound of the invention is applied to the column and the column is incubated for 30 min. The column is washed with 10 column volumes of binding buffer.

The invention claimed is:

1. An L-threo-β-benzyloxyaspartate derivative having a substituent on the benzene ring, represented by the following formula (1):

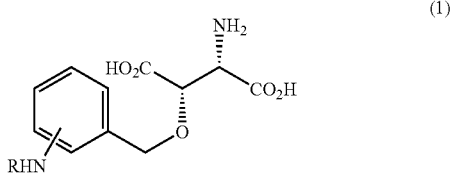

or a salt thereof,
wherein R is hydrogen, a linear or branched lower aliphatic acyl group with the acyl portion optionally substituted, an alicyclic acyl group, an aromatic acyl group with a substituent on the aromatic ring, an amino acid-derived group or a biotin derivative-derived group.

2. A compound according to claim 1, wherein R is hydrogen, an optionally thiol-substituted linear or branched lower aliphatic acyl group, an alicyclic acyl group, an aromatic acyl group optionally with a substituent on the aromatic ring, or a hydroxyl- or thiol-containing amino acid-derived group.

3. A compound according to claim 1, wherein R is acetyl, propionyl, n-butanoyl, sec-butanoyl, n-pentanoyl, pivaloyl, phenylacetyl, cyclohexylcarbonyl, benzoyl, substituted benzoyl, naphthoyl or pyridylcarbonyl.

4. A compound according to claim 1, wherein R is glycyl, alanyl, β-alanyl or cysteinyl.

5. A compound according to claim 1, wherein R is biotinyl or biotinyl-β-alanyl.

6. A compound according to claim 3, wherein R is a benzoyl group substituted with one or more substituents selected from the group consisting of an optionally substituted alkoxy group, an optionally substituted alkyl group, an optionally substituted aryl group, a cyano group, a nitro group, and a halogen atom.

7. A compound according to claim 6, wherein said substituent on the benzoyl group contains an isotope.

8. A method for producing an L-threo-nitrobenzylated (2S,3R) compound represented by the following formula (7):

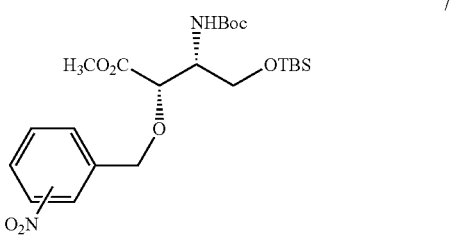

wherein Boc represents t-butoxycarbonyl and TBS represents t-butyldimethylsilyl, wherein a compound of formula (6) as defined in claim 6 is reacted with nitrobenzyl bromide in the presence of sodium hydride and tetra-n-butylammonium iodide without altering the stereospecificity.

9. The method of claim 8, wherein the yield of the L-threo-nitrobenzylated (2S,3R) compound represented by formula (7) is at least 70%.

10. The method of claim 8, which further comprises a step of producing a an L-threo-β-benzyloxyaspartate derivative having a substituent on the benzene ring, represented by the following formula (1):

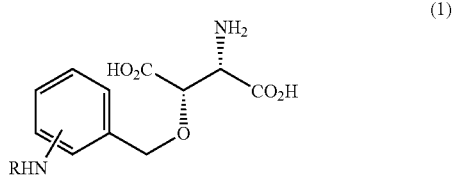

or a salt thereof,
wherein R is hydrogen, a linear or branched lower aliphatic acyl group with the acyl portion optionally substituted, an alicyclic acyl group, an aromatic acyl group with a substituent on the aromatic ring, an amino acid-derived group or a biotin derivative-derived group, by converting the $NO_2$ group on the benzene ring of the compound of formula (7) to an NHR group, and removing any protecting groups.

11. A compound represented by the following formula (7):

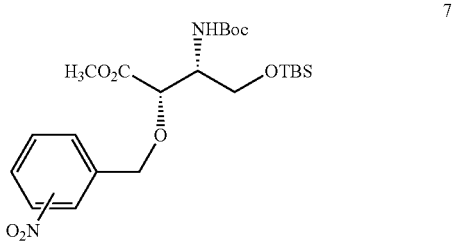

wherein Boc represents t-butoxycarbonyl and TBS represents t-butyldimethylsilyl.

12. A method for treating an L-glutamate-transporter-related neurodegenerative disease in a mammal, comprising administering to said mammal a pharmaceutical composition comprising an effective amount of a compound or a salt thereof as defined in formula (1) in claim 1, and a pharmaceutically acceptable carrier, wherein the L-glutamate-transporter-related neurodegenerative disease is selected from the group consisting of epilepsy, amyotrophic lateral sclerosis and Alzheimer's disease.

13. A pharmaceutical composition comprising an effective amount of a compound or a salt thereof as defined in formula (1) in claim 1, and a pharmaceutically acceptable carrier.

14. A method for inhibiting an L-glutamate-transporter, comprising administering an effective amount of a compound or a salt thereof as defined in claim 12.

15. A method for inhibiting L-glutamate uptake, comprising administering an effective amount of a compound or a salt thereof as defined in claim 12.

* * * * *